US007544507B2

(12) United States Patent
Yun et al.

(10) Patent No.: US 7,544,507 B2
(45) Date of Patent: Jun. 9, 2009

(54) MICROFLUIDIC CHIP FOR HIGH-THROUGHPUT SCREENING AND HIGH-THROUGHPUT ASSAY

(75) Inventors: Kwang-Seok Yun, Seoul (KR); Eui Sik Yoon, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 1014 days.

(21) Appl. No.: 10/956,486

(22) Filed: Oct. 4, 2004

(65) Prior Publication Data

US 2005/0226781 A1 Oct. 13, 2005

(30) Foreign Application Priority Data

Apr. 1, 2004 (KR) ...................... 10-2004-0022474

(51) Int. Cl.
*C12M 1/34* (2006.01)
*C12M 1/00* (2006.01)

(52) U.S. Cl. ................. 435/288.5; 422/100; 435/287.1; 435/287.2

(58) Field of Classification Search ... 435/287.1–288.5; 422/100
See application file for complete search history.

(56) References Cited

U.S. PATENT DOCUMENTS

2003/0215941 A1* 11/2003 Campbell et al. ........... 435/325
2004/0175708 A1* 9/2004 Caillat et al. .................... 435/6

OTHER PUBLICATIONS

Kwang-Seok Yun and Euisik Yoon, A Micro/Nano-Fluidic Chip-Based Micro-Well Array for High-Throughput Cellanalysis and Drug Screening, Micro Total Analysis Systems 2003, Oct. 5-9, 2003, p. 861-p. 864. vol. 1. The Transducers Research Foundation, Squaw Valley, California, USA.

* cited by examiner

*Primary Examiner*—Walter D Griffin
*Assistant Examiner*—Shanta G Doe
(74) *Attorney, Agent, or Firm*—Global IP Counselors, LLP

(57) ABSTRACT

Disclosed is a micro-fluidic chip for high-throughput screening and high-throughput assay, in which its structure is improved, thereby enhancing the efficiency of high-throughput screening and high-throughput assay. The micro-fluidic chip includes a well for isolating a specimen. The well can be arranged in a one- or two-dimension. A specimen-isolating means is disposed above the well and is movable upwards and downwards. An opening and closing means for moving the specimen-isolating means upwards and downwards is disposed above the specimen-isolating means. An inlet for injection the specimen and an outlet for discharging an excess of the injected specimen are provided. A reagent-injecting passage for injecting a reagent and a reagent-discharging passage for discharging the reagent are also provided.

19 Claims, 4 Drawing Sheets

MICROFLUIDIC CHIP FOR HIGH-THROUGHPUT SCREENING AND HIGH-THROUGHPUT ASSAY

BACKGROUND OF THE INVENTION

1. Field of the Invention

The present invention relates to a micro-fluidic chip, particularly to such a chip for high-throughput screening and high-throughput assay, in which its structure is improved, thereby enhancing the efficiency of high-throughput screening and high-throughput assay.

2. Background of the Related Art

In general, a well plate has been used for biological and chemical experiments. There are a 16-well plate, a 48-well plate or a 96-well plate depending on the number of wells. Recently, a plate having more than 1536 wells has been introduced for a high-throughput assay.

Further, the advancement in micro-machining technique facilitates the development of micro-fluidic chips for a high-throughput assay. U.S. Pat. No. 6,235,520 B1 discloses a micro-fluidic chip having a high degree of integration. However, only the highly integrated structure would not help injecting a reagent into each individual well independently.

Also, an article, “Microfluidic device for single-cell analysis” A. R. Wheeler; Analytical Chemistry, Vol. 75, pp. 3581-3586, 2003, has proposed a chip in which a cell is immobilized at a desired place, and a reagent is injected through a fluid passage. However, it has disadvantages in that the cell cannot be stably held in place in absence of fluid flow and many numbers of cells cannot be analyzed at the same time due to its one-dimensional configuration.

The above-described conventional micro-fluidic chip has increased only its degree of integration, and thus additional control devices are required for loading a specimen and reagent into the highly-integrated wells. Furthermore, in the case where the specimen and reagent are a fluid, its amount is reduced due to the high integration and thus easily evaporated.

SUMMARY OF THE INVENTION

Therefore, the present invention has been made in view of the above problems occurring in the prior art, and it is an object of the present invention to provide a micro-fluidic chip, in which different reagents can be injected into respective different wells.

Another object of the present invention is to provide a micro-fluidic chip, in which wells can be arranged in a two-dimensional pattern and thus a degree of integration can be improved.

Another object of the present invention is to provide a micro-fluidic chip, in which a specimen or reagent can be isolated inside the well and be prevented from evaporating outside the well.

Another object of the present invention is to provide a micro-fluidic chip, in which a pair of electrode is disposed inside the well, thereby enabling an easy injection of reagent into the well by means of dielectrophoresis phenomena.

Another object of the present invention is to provide a micro-fluidic chip, in which an electric reaction can be detected using an electrode disposed inside the well.

To accomplish the above objects, according to one aspect of the present invention, there is provided a micro-fluidic chip for high-throughput screening and high-throughput assay. The micro-fluidic chip of the invention comprises: a) a well for isolating a specimen, the well being capable of being arranged in a one- or two-dimension; b) a specimen-isolating means disposed above the well and movable upwards and downwards; c) an opening and closing means disposed above the specimen-isolating means and for moving the specimen-isolating means upwards and downwards; d) an inlet for injection the specimen and an outlet for discharging an excess of the injected specimen; and e) a reagent-injecting passage for injecting a reagent and a reagent-discharging passage for discharging the reagent.

According to the invention, the well is highly integrated in the micro-fluidic chip in a one- or two-dimensional fashion. In addition, the specimen-isolating means isolates the specimen and reagent inside the well and prevents them from evaporating. The opening and closing means opens and closes the specimen-isolating means. Furthermore, the reagent-injecting passage is formed at each well such that the reagent is selectively injected. In this way, the micro-fluidic chip of the invention can perform high-throughput screening and high-throughput assay more efficiently.

According to another aspect of the invention, there is also provided a micro-fluidic chip for high-throughput screening and high-throughput assay. The micro-fluidic chip of the invention comprises: a) a well for isolating a specimen, the well being capable of being arranged in a one- or two-dimension; b) a specimen-isolating means disposed above the well and movable upwards and downwards; c) an opening and closing means disposed above the specimen-isolating means and for moving the specimen-isolating means upwards and downwards; d) an inlet for injection the specimen and an outlet for discharging an excess of the injected specimen; e) a reagent-injecting passage for injecting a reagent and a reagent-discharging passage for discharging the reagent; and f) a pair of metal electrode formed inside the well and causing a dielectrophoresis phenomena.

According to the invention, a pair of electrodes is disposed inside of each well, so that the specimen can be easily entrapped into the inside of the well, using the dielectrophoresis phenomena. Furthermore, the electrode can be used for detecting the electric reaction of the specimen.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will now made in detail to the preferred embodiment of the present invention with reference to the attached drawings.

Figure 1A:
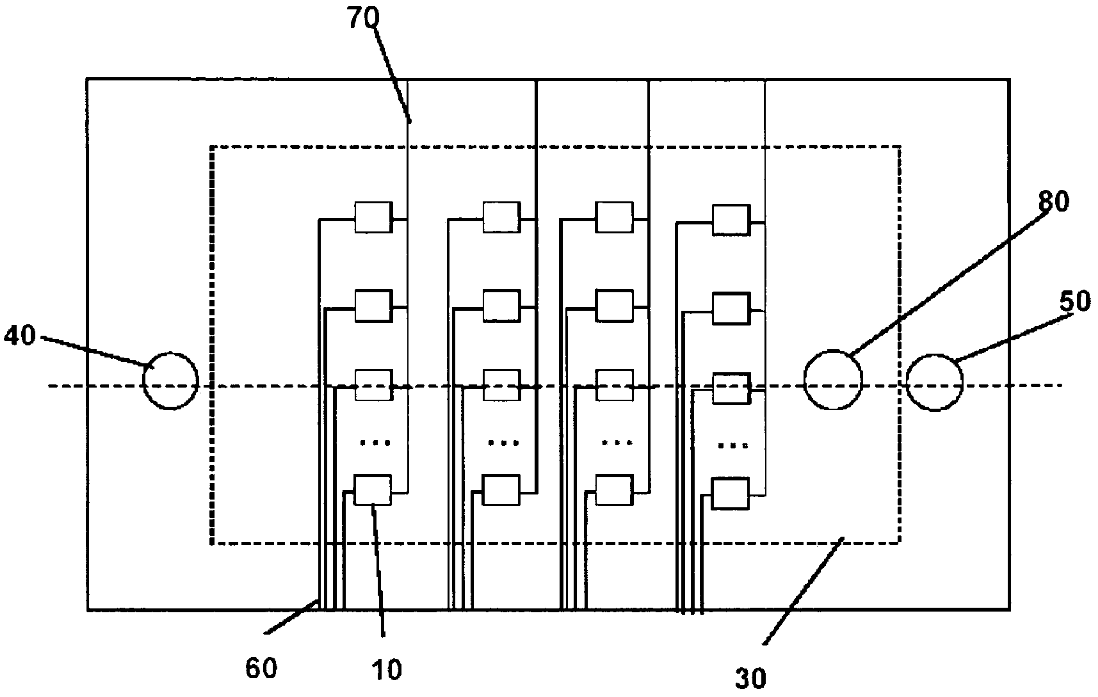
FIG. 1*a* is a plan view schematically showing a micro-fluidic chip according to a first embodiment of the invention.
Figure 1B:
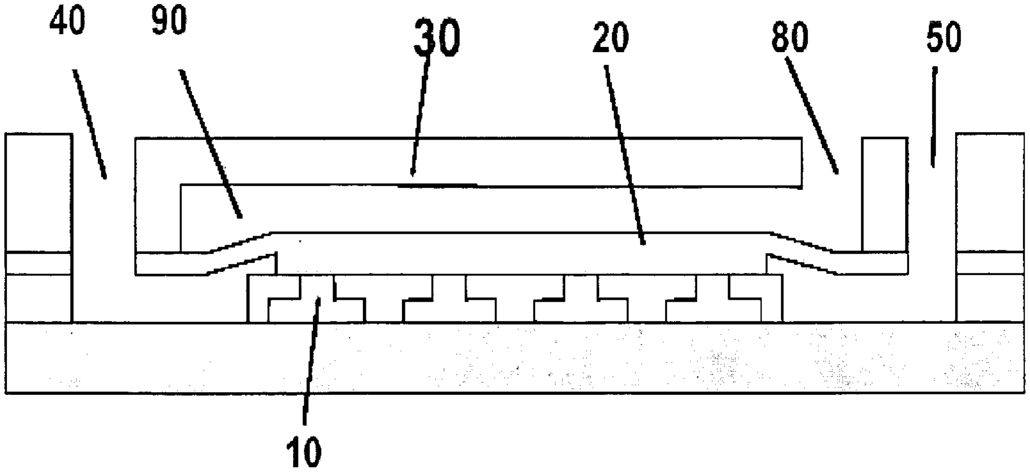
FIG. 1*b* is a cross-sectional view schematically showing a micro-fluidic chip according to a first embodiment of the invention.

FIGS. 1a and 1b are respectively a plan view and a cross-sectional view schematically showing a micro-fluidic chip according to a first embodiment of the invention.

As shown in FIGS. 1a and 1b, the micro-fluidic chip comprises a well 10, a specimen isolating means 20, an opening and closing means 30, an inlet 40, an outlet 50, a reagent-injecting passage 60, and a reagent-discharging passage 70.

The well 10 is arranged in one- or two-dimension, in which a specimen such as a cell, a bead or a solution is placed. Also, a reagent is injected thereto in order to detect a reaction with the specimen.

In addition, the wells 10 may be extended endlessly in a two-dimensional plane. Furthermore, the two-dimensional arrangement of the wells 10 may be carried out in a patterned or non-patterned fashion.

Also, the amount or number of isolated specimen to be injected into the well 10 can be varied with the size of the well 10.

The specimen-isolating means 20 is disposed above the well 10, and movable upwards and downwards to thereby be able to isolate the specimen placed inside the well 10. The specimen and reagent are isolated inside the well 10 so that they are prevented from escaping or evaporating outside the well and entering neighboring wells.

The opening and closing means 30 is disposed at the upper end of the specimen-isolating means 20, and opens or closes the well 10 by moving upwards and downwards the specimen-isolating means 20. The opening and closing means 30 is provided with a space 90 formed therein to place the specimen-isolating means upwardly.

According to the first embodiment of the invention, the opening and closing means 30 is provided with a pneumatic passage 80, and the specimen-isolating means 20 is opened and closed by an air pressure through the pneumatic passage 80. In FIG. 1, the pneumatic passage 80 is disposed centrally at the left side of the opening and closing means 30, but may be disposed at any position of the opening and closing means 30. The opening and closing means 30 having the pneumatic passage 80 will be hereinafter described in greater detail.

The specimen is injected into the inside of the micro-fluidic chip from the inlet 40, and a certain amount of the specimen is entered into the inside of the well. Then, the remaining excessive portion of the injected specimen is discharged through the outlet 50.

The reagent-injecting passage 60 is a passageway through which a reagent is injected into the wells 10. The reagent-injecting passage 60 is communicated with each well 10 through different channels. Therefore, the same or different reagents can be injected through the channels to the respective wells from the reagent-injecting passage 60.

The superfluous reagent excepting a certain amount required for the reaction is discharged through the reagent-discharging passage 70, also through which the reagent used for the reaction is discharged. In FIG. 1a, the reagent-discharging passage 70 is formed as the same channel, but may be embodied in different channels.

Figure 2:
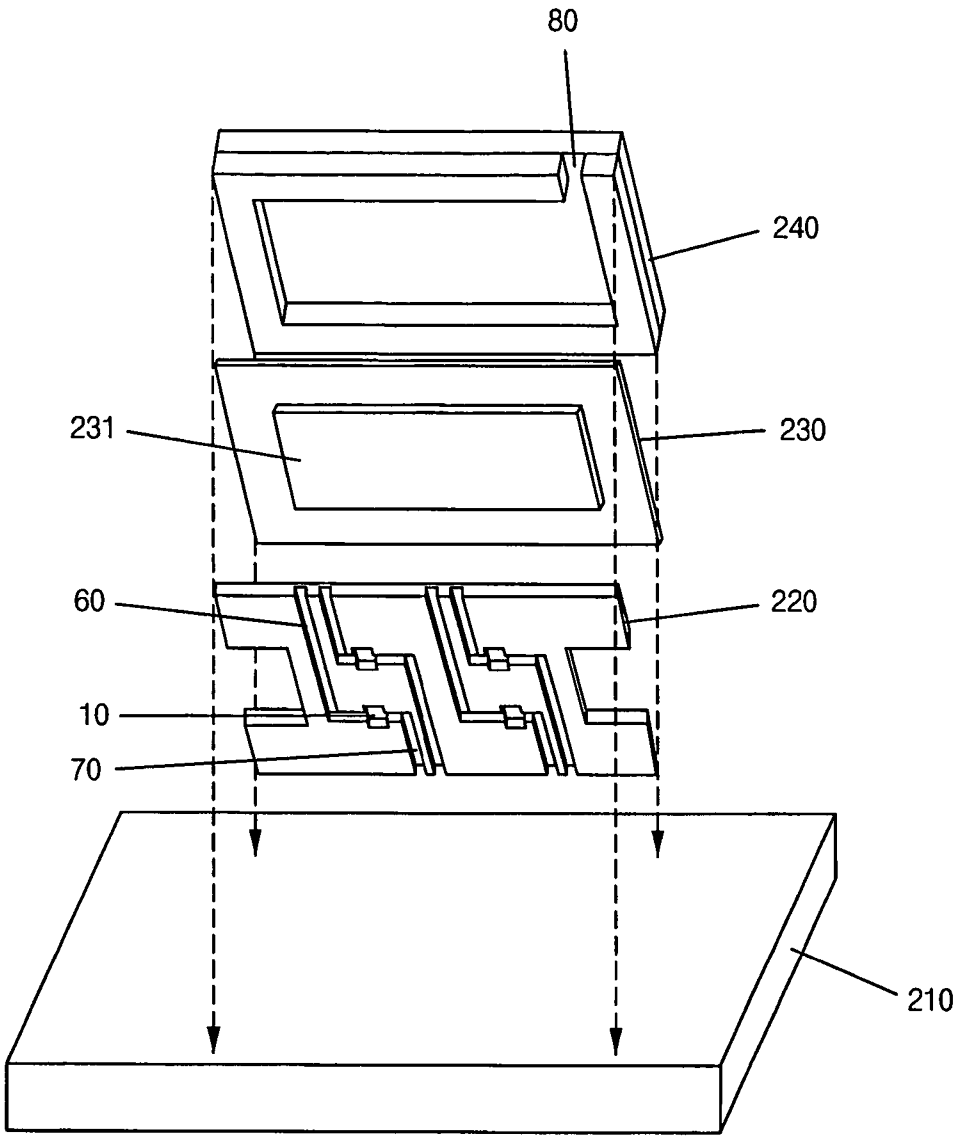
FIG. 2 is a perspective exploded view of the micro-fluidic chip according to the first embodiment of the invention.

FIG. 2 is a perspective exploded view of the micro-fluidic chip according to the first embodiment of the invention. As shown in FIG. 2, the micro-fluidic chip of this embodiment is formed of four substrates combined with each other.

A first substrate 210 is provided as a base of the micro-fluidic chip.

Above the first substrate 210 is provided a second substrate 220. The second substrate 220 is provided with wells 10 arranged in a one- or two-dimensional pattern, and, at the lower end, with a reagent-injecting passage 60 and a reagent-discharging passage 70 connected to the well 10.

Above the second substrate 220 is disposed a third substrate 230. Here, the third substrate 230 has the form of a thin cover 231 and serves as the specimen-isolating means 20.

A fourth substrate 240 is disposed above the third substrate 230. The fourth substrate 240 is provided with an empty space thereinside. In addition, the fourth substrate 240 is constructed such that the third substrate 231 can be lifted or descended by an air pressure through the pneumatic passage 80. That is, the fourth substrate 240 functions as an opening and closing means 30.

Here, the micro-fluidic chip of the invention may be fabricated by forming four or more substrates and combining them, or any two or more of the above substrates may be formed of one unitary substrate and combined into the micro-fluidic chip of the invention.

The micro-fluidic chip of the invention may be fabricated using the semi-conductor process or the microelectro-mechanical Systems (MEMS) technique.

The respective substrates described above may be formed of various materials, such as silicon, glass, PDMS (polydimethilsiloxane), silicon rubber, or other polymers.

Figure 3:
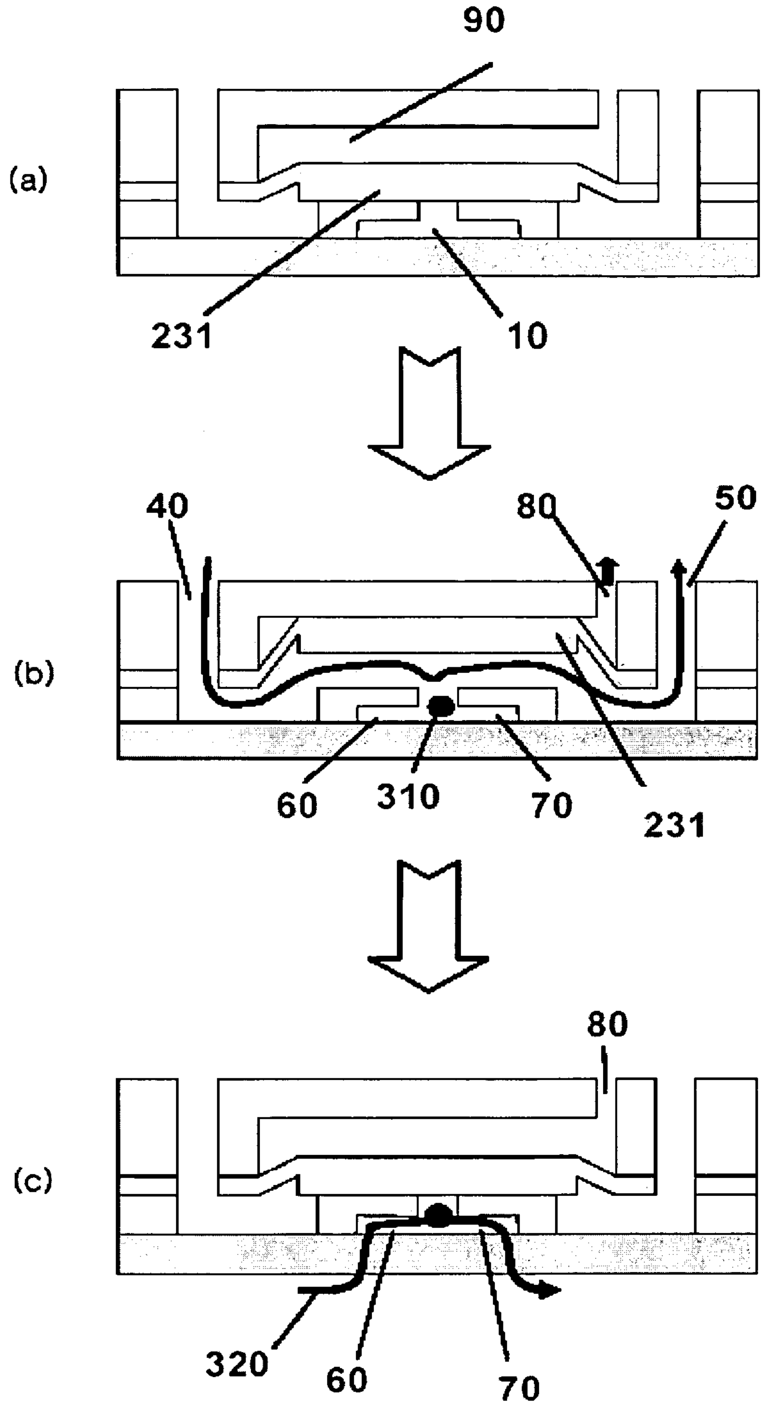
FIG. 3 shows an operation of the micro-fluidic chip according to the first embodiment of the invention.

FIG. 3 shows an operation of the micro-fluidic chip according to the first embodiment of the invention. As shown in FIG. 3(a), first, the cover 231 as a specimen-isolating means has a downwardly convex shape. In this way, the cover 231 is pressed downwardly by a certain magnitude of force due to its convexity so that the respective wells 10 can be isolated.

Afterwards, as shown in FIG. 3(b), an air is suctioned through the pneumatic passage 80 and transferred into the empty space 90 above the cover 231.

Then, a specimen is injected through the inlet 40. The injected specimen is discharged towards the outlet 50, and simultaneously in part flows towards the reagent-discharging passage 70. Here, since the size of the reagent-discharging passage 70 is smaller than that of the specimen, the specimen such as cells, beads, or the like cannot be discharged through the reagent-discharging passage 70, but trapped inside the well 10.

When a certain amount of the specimen 310 is injected into the inside of the well 10, the reagent-discharging passage 70 is more or less blocked such that the amount of the specimen exiting therethrough is reduced. Therefore, after that, the specimen entering through the inlet 40 can no longer flow towards the well containing a specimen, but flows out towards the outlet 50.

Here, the amount or number of specimen 310 to be injected and isolated inside the well 10 may be varied with the size of the well 10.

Next, as shown in FIG. 3(c), an air is injected through the pneumatic passage 80 into the opening and closing means 30 to again move the cover 231 downwardly. That is, the specimen 310 inside the well 10 is isolated by blocking the upper portion of the well 10.

Then, a reagent 320 needed for reaction is injected through the reagent-injecting passage 60, and thus, a desired experiment can be carried out inside the well 10. Here, the injected reagent 320 can be prevented from entering neighboring wells since the upper portion thereof is blocked. Also, different reagents can be injected into different wells through different channels of the reagent-injection passage 60. The injected reagent 320 can only be discharged through the reagent-discharging passage 70.

As described above, in the first embodiment of the invention, the opening and closing means is provided with a pneumatic passage, and the isolating means is configured to be opened and closed by an air pressure through the pneumatic passage 80.

In addition, the specimen-isolating means and the opening and closing means are provided with a metal electrode so that the isolating means can be opened and closed by an electric field, which is electrically controlled.

Furthermore, the specimen-isolating means and the opening and closing means are provided with a conductor line formed therein, such that the isolating means can be opened and closed by an electromagnetic field, which is electrically controlled.

Also, the opening and closing means is provided with an electrode formed therein, and the specimen isolating means is provided with a piezoelectric device, so that the isolating means can be opened and closed by an application of external voltage.

Figure 4:
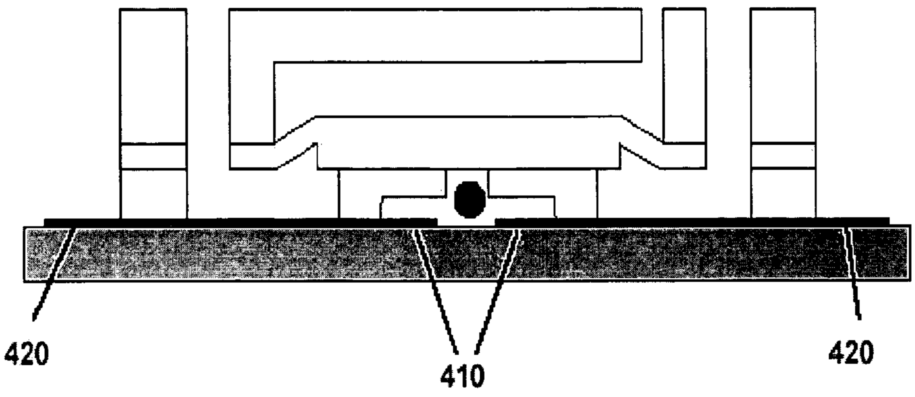
FIG. 4 shows a cross-section of a micro-fluidic chip according to a second embodiment of the invention.

FIG. 4 shows a cross-section of a micro-fluidic chip according to a second embodiment of the invention. As shown in FIG. 4, similar to the first embodiment, the micro-fluidic chip of this embodiment comprises a well 10, a specimen isolating means 20, an opening and closing means, an inlet 40, an outlet 50, a reagent-injecting passage 60, and a reagent-discharging passage 70. In addition, each of the wells is provided with a pair of electrodes 410 formed thereinside.

Application of voltage to the pair of electrodes enables the specimen to be attracted into the well or to be pushed away therefrom. This action is caused by dielectrophoresis phenomena.

The dielectrophoresis phenomena can be described by that a particle such as a cell and a bead is forced into an area of dense electric field, or towards a region of weak electric field. Here, the mobility of particle varies with the type of the solution or the particles, and also can be controlled by varying the magnitude and frequency of applied electric field. Using the dielectrophoresis phenomena, only required cell or bead from the specimen can be introduced into the inside of a particular well 10.

In addition, the metal electrode 410 may exert an electric stimulation to the specimen inside the well. For example, in case where the specimen is a cell, a study on a particular disease such as a nervous disorder can by performed by observing the reaction of the cell to an electric stimulation externally applied. Also, a hole can be formed in a cell by applying externally an electric field, and through the hole a reagent, DNA or the like can be introduced.

Furthermore, the metal electrode 410 may detect an electric signal of the reaction produced inside the well. For example, a membrane potential can be detected by the metal electrode. Also, an oxidation and reduction method can be used in that the metal electrode applies an appropriate voltage or current and detects a signal in response to the applied voltage or current.

Here, the metal electrode according to the second embodiment of the invention may be extended into the outside thereof to thereby form a pad 420, through which an electric signal can be applied or detected.

The metal electrode 410 is preferred to be formed of one of gold, silver, platinum, aluminum, semiconductor material or conductive polymer.

The second embodiment of the invention can obtain the same effects as in the first embodiment, by applying in the same way a two-dimensional arrangement, the amount or number of specimen according to the size of the well, the channel of the reagent-injection passage, the reagent to be injected, and the empty space of the isolating means. The detailed explanation of the above application is previously made in conjunction with the first embodiment of the invention, and thus will not be repeated here.

In addition, similar to the first embodiment, the second embodiment may employ various types of opening and closing means, such as by an air pressure, an electric field, an electromagnetic field, or a piezoelectric element.

Figure 5:
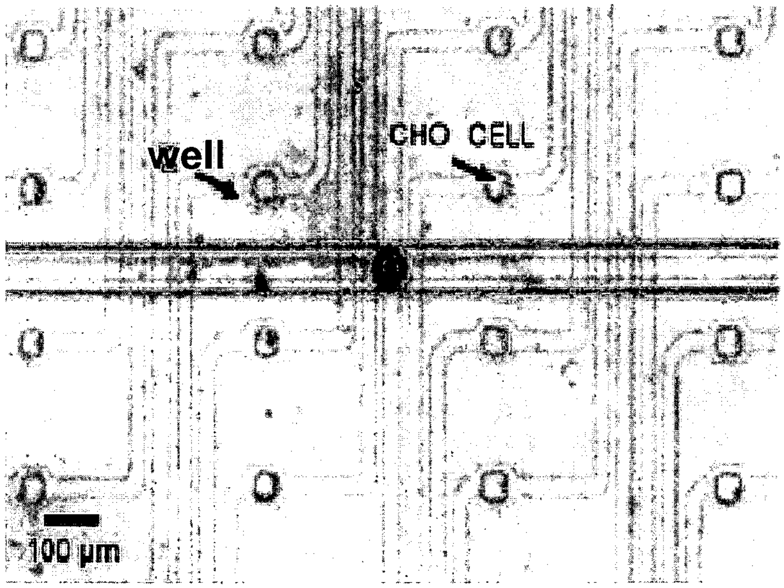
FIG. 5 is a photograph showing a micro-fluidic chip fabricated according to the first embodiment of the invention.

FIG. 5 is a photograph showing an actual micro-fluidic chip according to the first embodiment of the invention. FIG. 5 is a photograph of a real micro-fluidic chip of the invention, which is fabricated using a semiconductor processing and MEMS technique (International micro TAS conference 2003).

As shown in FIG. 5, the micro-fluidic chip has sixteen wells of 4×4 array, each of which has a CHO(Chinese hamster ovary) cell isolated therein.

As described above, the micro-fluidic chip of the invention has various effects as follows:

First, using a semiconductor processing and MEMS technique the wells can be highly integrated into a chip, thereby performing many experiments and analyses at the same time.

Second, a specimen-isolating means is provided above the wells, thereby enabling a stable isolation of the specimen such as a cell, a bead or the like inside the well. In addition, a cover for the specimen-isolating means is disposed above the wells, so that a reagent flown into the respective wells can be prevented from leaking into neighboring wells.

Third, reagent-injecting passages connected to the respective wells are provided, so that different reagents can be flown into different wells, thereby carrying out, at the same time, different experiments in different wells.

Fourth, a pair of metal electrodes is disposed inside each well, so that the specimen can be attracted inward the well or pushed away therefrom by the dielectrophoresis phenomena. In addition, an electric stimulation can be exerted to the specimen inside the well through the electrode to thereby be able to electrically detect the reaction being occurred inside the well.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A micro-fluidic chip for high-throughput screening and high-throughput assay, the micro-fluidic chip comprising:

a well for isolating a specimen, the well being arranged in a one- or two-dimension; a specimen-isolating means being disposed above the well and movable upwards and downwards;

an opening and closing means being disposed above the specimen-isolating means and for moving the specimen-isolating means upwards and downwards, the opening and closing means being provided with a pneumatic passage, the specimen-isolating means being opened and closed by controlling an external pressure through the pneumatic passage;

an inlet for injecting the specimen and an outlet for discharging an excess of the injected specimen; and a reagent-injecting passage for injecting a reagent and a reagent-discharging passage for discharging the reagent.

2. A micro-fluidic chip according to claim 1, wherein the two-dimensional array of the well is positioned in a patterned or non-patterned fashion.

3. A micro-fluidic chip according to claim 1, wherein the amount and number of specimen to be injected and isolated are determined depending on the size of well.

4. A micro-fluidic chip according to claim 1, further comprising a plurality of wells and reagent-injecting passages, wherein each reagent-injecting passage connected respectively to each well is formed of a channel different from the other reagent-injecting passages.

5. A micro-fluidic chip according to claim 4, wherein a same reagent or different reagents are injected through each of the channels of the reagent-injecting passages, each of which is connected respectively to one of the wells.

6. A micro-fluidic chip according to claim 1, wherein the opening and closing means includes a space for positioning the specimen-isolating means upwards.

7. A micro-fluidic chip according to claim 1, wherein the specimen-isolating means and the opening and closing means are provided with a metal electrode and the specimen-isolating means is opened and closed by means of an electric field being electrically controlled.

8. A micro-fluidic chip according to claim 1, wherein the specimen-isolating means and the opening and closing means are provided with a conductor line formed therein and the specimen-isolating means is opened and closed by means of an electromagnetic field being electrically controlled.

9. A micro-fluidic chip according to claim 1, wherein the opening and closing means are provided with a metal electrode and the specimen-isolating means is provided with a piezoelectric element, so that the specimen-isolating means is opened and closed by means of an application of external voltage.

10. A micro-fluidic chip for high-throughput screening and high-throughput assay, the micro-fluidic chip comprising:

a well for isolating a specimen, the well being configured to be arranged in a one- or two-dimension;

a specimen-isolating means being disposed above the well and movable upwards and downwards;

an opening and closing means being disposed above the specimen-isolating means and for moving the specimen-isolating means upwards and downwards, the opening and closing means being provided with a pneumatic passage, the specimen-isolating means being opened and closed by controlling an external pressure through the pneumatic passage;

an inlet for injecting the specimen and an outlet for discharging an excess of the injected specimen;

a reagent-injecting passage for injecting a reagent and a reagent-discharging passage for discharging the reagent; and a pair of metal electrode formed inside the well and causing a dielectrophoresis phenomena.

11. A micro-fluidic chip according to claim 10, wherein the metal electrode is formed of one of gold, silver, platinum, aluminum, semiconductor material, or conductive polymer.

12. A micro-fluidic chip according to claim 10, wherein the well is arranged in a two-dimensional array positioned in a patterned or non-patterned fashion.

13. A micro-fluidic chip according to claim 10, wherein the amount and number of specimen to be injected and isolated is determined depending on the size of well.

14. A micro-fluidic chip according to claim 10, further comprising a plurality of wells and reagent-injecting passages, wherein each reagent-injecting passage connected respectively to each well is formed of a channel different from the other reagent-injecting passages.

15. A micro-fluidic chip according to claim 14, wherein a same reagent or different reagents are injected through each of the channels of the reagent-injecting passages, each of which is connected respectively to one of the wells.

16. A micro-fluidic chip according to claim 10, wherein the opening and closing means includes a space for positioning the specimen-isolating means upwards.

17. A micro-fluidic chip according to claim 10, wherein the specimen-isolating means and the opening and closing means are provided with a metal electrode and the specimen-isolating means is opened and closed by means of an electric field being electrically controlled.

18. A micro-fluidic chip according to claim 10, wherein the specimen-isolating means and the opening and closing means are provided with a conductor line formed therein and the specimen-isolating means is opened and closed by means of an electromagnetic field being electrically controlled.

19. A micro-fluidic chip according to claim 10, wherein the opening and closing means are provided with a metal electrode and the specimen-isolating means is provided with a piezoelectric element, so that the specimen-isolating means is opened and closed by means of an application of external voltage.

* * * * *